US012110275B2

(12) United States Patent
Buckley et al.

(10) Patent No.: US 12,110,275 B2
(45) Date of Patent: *Oct. 8, 2024

(54) METHODS OF SYNTHESIZING 2-[4-[(2,3,4-TRIMETHOXYPHENYL)METHYL] PIPERAZIN-1-YL]ETHYL PYRIDINE-3-CARBOXYLATE

(71) Applicant: IMBRIA PHARMACEUTICALS, INC., Boston, MA (US)

(72) Inventors: Neil Buckley, Boston, MA (US); Dan Belmont, Boston, MA (US); Bryan Hauser, Boston, MA (US); Myoung Goo Kim, Boston, MA (US); Kumar Kannan, Boston, MA (US)

(73) Assignee: IMBRIA PHARMACEUTICALS, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/239,337

(22) Filed: Aug. 29, 2023

(65) Prior Publication Data

US 2023/0399300 A1    Dec. 14, 2023

Related U.S. Application Data

(63) Continuation of application No. 17/359,762, filed on Jun. 28, 2021, now Pat. No. 11,780,811.

(60) Provisional application No. 63/046,123, filed on Jun. 30, 2020.

(51) Int. Cl.
*C07D 213/803*    (2006.01)

(52) U.S. Cl.
CPC ............................. *C07D 213/803* (2013.01)

(58) Field of Classification Search
CPC .................................................. C07D 213/803
USPC ....................................................... 544/365
See application file for complete search history.

(56) References Cited

U.S. PATENT DOCUMENTS

| | | |
|---|---|---|
| 4,100,285 A | 7/1978 | Murai et al. |
| 4,166,452 A | 9/1979 | Generales, Jr. |
| 4,256,108 A | 3/1981 | Theeuwes |
| 4,265,874 A | 5/1981 | Bonsen et al. |
| 4,574,156 A | 3/1986 | Morita et al. |
| 4,845,099 A | 7/1989 | Ruger et al. |
| 4,876,257 A | 10/1989 | Hajos et al. |
| 4,885,300 A | 12/1989 | Press et al. |
| 5,077,288 A | 12/1991 | Lavielle et al. |
| 5,286,728 A | 2/1994 | Ferrini |
| 5,340,809 A | 8/1994 | Gaudry et al. |
| 5,380,726 A | 1/1995 | Ferrini |
| 5,384,319 A | 1/1995 | Ferrini |
| 5,397,780 A | 3/1995 | Mizuno et al. |
| 5,399,557 A | 3/1995 | Mizuno et al. |
| 5,401,743 A | 3/1995 | Rendenbach-Mueller et al. |
| 5,428,038 A | 6/1995 | Chatterjee et al. |
| 5,527,800 A | 6/1996 | Goto et al. |
| 5,591,849 A | 1/1997 | Kato et al. |
| 5,641,779 A | 6/1997 | Halazy et al. |
| 5,770,735 A | 6/1998 | Emonds-Alt et al. |
| 5,776,937 A | 7/1998 | Gante et al. |
| 5,849,745 A | 12/1998 | Wierzbicki et al. |
| 5,856,326 A | 1/1999 | Anthony et al. |
| 5,962,448 A | 10/1999 | Mizuno et al. |
| 5,977,111 A | 11/1999 | Mizuno et al. |
| 6,087,346 A | 7/2000 | Glennon et al. |
| 6,121,267 A | 9/2000 | Glase et al. |
| 6,200,989 B1 | 3/2001 | De Cillis et al. |
| 6,214,841 B1 | 4/2001 | Jackson et al. |
| 6,271,223 B1 | 8/2001 | Mizuno et al. |
| 6,331,623 B1 | 12/2001 | Mizuno et al. |
| 6,528,529 B1 | 3/2003 | Brann et al. |
| 6,562,978 B1 | 5/2003 | Imamura et al. |
| 6,693,099 B2 | 2/2004 | Degenhardt et al. |
| 7,638,531 B2 | 12/2009 | Mutahi et al. |
| 7,666,866 B2 | 2/2010 | Franiskovich et al. |
| 7,772,251 B2 | 8/2010 | Sturzebecher et al. |
| 7,968,538 B2 | 6/2011 | Becker et al. |
| 8,016,783 B2 | 9/2011 | Pastore et al. |
| 8,202,901 B2 | 6/2012 | Lopaschuk et al. |
| 8,461,117 B2 | 6/2013 | Sufi et al. |
| 8,569,495 B2 | 10/2013 | Chassaing et al. |
| 8,697,661 B2 | 4/2014 | Kritikou |
| 9,096,538 B2 | 8/2015 | Nakamura et al. |
| 9,120,801 B2 | 9/2015 | Alisi et al. |

(Continued)

FOREIGN PATENT DOCUMENTS

| | | |
|---|---|---|
| CA | 2170615 A1 | 3/1995 |
| CA | 2186010 A1 | 9/1995 |

(Continued)

OTHER PUBLICATIONS

Abrahamsson, 1998, In vitro and in vivo erosion of two different hydrophilic gel matrix tablets, European Journal of Pharmaceuticals and Biopharmaceutics, 46:69-75.
Aswathy, 2018, Formulation and Evaluaton of Mucoadhesive Buccal Tablet of Antianginal Drug, IJPPR. Human Journals, 13(1):43-71.
Bhosle, 2006, Mutual Prodrug Concept: Fundamentals and Applications, Indian Journal of Pharmaceutical Sciences, May-June, pp. 286-294.
Cheng, 2006, Discovery of Potent and Orally Available Malonyl-CoA Decarboxylase Inhibitors as Cardioprotective Agents, J. Med. Chem. 49:4055-4058.

(Continued)

*Primary Examiner* — Taofiq A Solola
(74) *Attorney, Agent, or Firm* — Brown Rudnick LLP; Adam M. Schoen

(57) ABSTRACT

The invention provides methods of chemical synthesis of the pharmacological agent 2-[4-[(2,3,4-trimethoxyphenyl)methyl]piperazin-1-yl]ethyl pyridine-3-carboxylate, also called CV-8972. The methods entail formation of a free base form of 2-[4-[(2,3,4-trimethoxyphenyl)methyl]piperazin-1-yl]ethanol, also called CV-8814, as intermediate without producing a salt form of CV-8814.

14 Claims, No Drawings

(56) References Cited

U.S. PATENT DOCUMENTS

| | | | |
|---|---|---|---|
| 10,167,258 B2 | 1/2019 | Chuang et al. | |
| 10,556,013 B2 | 2/2020 | Levin | |
| 10,918,728 B2 | 2/2021 | Levin | |
| 10,953,102 B2 | 3/2021 | Levin | |
| 11,376,330 B2 | 7/2022 | Levin | |
| 11,780,811 B2* | 10/2023 | Buckley | C07D 213/803 544/365 |
| 2003/0191182 A1 | 10/2003 | Lopaschuk et al. | |
| 2003/0232877 A1 | 12/2003 | Sikorski et al. | |
| 2004/0082564 A1 | 4/2004 | Arrhenius et al. | |
| 2005/0004121 A1 | 1/2005 | Palani et al. | |
| 2007/0004750 A1 | 1/2007 | Lorsbach et al. | |
| 2008/0108618 A1 | 5/2008 | Brann et al. | |
| 2008/0161400 A1 | 7/2008 | Virsik et al. | |
| 2009/0197891 A1 | 8/2009 | Lecanu et al. | |
| 2009/0258064 A1 | 10/2009 | Newell et al. | |
| 2010/0022530 A1 | 1/2010 | Schiemann et al. | |
| 2011/0046370 A1 | 2/2011 | Sim et al. | |
| 2011/0137362 A1 | 6/2011 | Foreman et al. | |
| 2011/0212072 A1 | 9/2011 | Henkel et al. | |
| 2012/0214818 A1 | 8/2012 | Dudley | |
| 2016/0060530 A1 | 3/2016 | Archetti et al. | |
| 2016/0346397 A1 | 12/2016 | Milne et al. | |
| 2017/0008950 A1 | 1/2017 | Capon | |
| 2017/0105414 A1 | 4/2017 | Nakano et al. | |
| 2018/0360975 A1 | 12/2018 | Levin | |
| 2019/0084917 A1 | 3/2019 | Savourey et al. | |
| 2019/0216936 A1 | 7/2019 | Levin | |
| 2020/0138963 A1 | 5/2020 | Levin | |
| 2021/0353617 A1 | 11/2021 | Levin et al. | |
| 2022/0249463 A1 | 8/2022 | Levin et al. | |

FOREIGN PATENT DOCUMENTS

| | | |
|---|---|---|
| CN | 101747292 B | 7/2011 |
| DE | 2714996 A1 | 10/1977 |
| EP | 0144991 A2 | 6/1985 |
| EP | 0251141 A1 | 1/1988 |
| EP | 615855 A1 | 9/1994 |
| EP | 661266 A1 | 7/1995 |
| EP | 749967 A1 | 12/1996 |
| EP | 1634598 A1 | 3/2006 |
| EP | 1886994 A1 | 2/2008 |
| EP | 2727916 A1 | 5/2014 |
| JP | S57131777 | 8/1982 |
| JP | 2000147773 A | 5/2000 |
| JP | 2006113343 A | 4/2006 |
| JP | 2015017236 A | 1/2015 |
| RU | 2377989 C2 | 1/2010 |
| WO | 1995000165 A1 | 1/1995 |
| WO | 9626196 A2 | 8/1996 |
| WO | 9630054 A1 | 10/1996 |
| WO | 9630343 A1 | 10/1996 |
| WO | 9728141 A1 | 8/1997 |
| WO | 9746549 A1 | 12/1997 |
| WO | 98/58638 A1 | 12/1998 |
| WO | 9950247 A1 | 10/1999 |
| WO | 2001005763 A2 | 1/2001 |
| WO | 2002058698 A2 | 8/2002 |
| WO | 2002064576 A1 | 8/2002 |
| WO | 2003006628 A2 | 1/2003 |
| WO | 2006027223 A1 | 3/2006 |
| WO | 2006117686 A2 | 11/2006 |
| WO | 2006133784 A1 | 12/2006 |
| WO | 2007075629 A2 | 7/2007 |
| WO | 2007096251 A1 | 8/2007 |
| WO | 2007/116074 A1 | 10/2007 |
| WO | 2007/116243 A2 | 10/2007 |
| WO | 2008109991 A1 | 9/2008 |
| WO | 2009015485 A1 | 2/2009 |
| WO | 2009/058818 A2 | 5/2009 |
| WO | 2009066315 A2 | 5/2009 |
| WO | 2009156479 A1 | 12/2009 |
| WO | 2011032099 A1 | 3/2011 |
| WO | 2012049101 A1 | 4/2012 |
| WO | 2015018660 A1 | 2/2015 |
| WO | 2016005576 A1 | 1/2016 |
| WO | 2016107603 A1 | 7/2016 |
| WO | 2018/236745 A1 | 12/2018 |
| WO | 2020/081361 A1 | 4/2020 |

OTHER PUBLICATIONS

Cheng, 2006, Synthesis and structure-activity relationship of small-molecule malonyl coenzyme A decarboxylase inhibitors, J. Med. Chem. 49:1517-1525.

DAS, 1995, Essential Fatty Acid Metabolism in Patients with Essential Hypertension, Diabetes Mellitus and Coronary Heart Disease, Prostaglandins Leukotrienes and Essential Fatty Acids, 52, 387-391.

Extended European Search Report issued in European Application No. 18821590.9, date of mailing: Oct. 5, 2020, 6 pages.

Extended European Search Report issued in European Application No. 19872680.4, date of mailing: Jun. 20, 2022, 7 pages.

Extended European Search Report issued in European Application No. 22169109.0, date of mailing: Aug. 30, 2022, 7 pages.

Fang, 2011. Therapeutic inhibition of fatty acid oxidation in right ventricular hypertrophy: exploiting Randle's cycle, Journal of Molecular Medicine, 90:31-43.

Fillmore, 2014, Malonyl CoA: A Promising Target for the Treatment of Cardiac Disease, Int. Union of Biochem. and Mol. Biol., 66(3):139-146.

Fillmore, 2014, Mitochondrial fatty acid oxidation alterations in heart failure, ischemic heart disease and diabetic cardiomyopathy, Brit. J. Pharmacol. 171:2080-2090.

Folmes, 2005, Fatty Acid Oxidation Inhibitors in the Management of Chronic Complications of Atherosclerosis, Current Atherosclerosis Reports 2005, 7, 63-70.

Gallaher, 1993, Viscosity and Fermentability as Attributes of Dietary Fiber Responsible of the Hypocholesterolemic Effect in Hamsters, J Nutr., 123, pp. 244-252.

Gao, 2011, Echocardiography in Mice. Curr Protoc Mouse Biol, 1:71-83.

Gibbs, 1995, Cardiac efficiency, Cardiovasc. Res. 30:627-634.

Gustafsson, 1999, Characterisation of particle properties and compaction behaviour of hydroxypropyl methylcellulose with different degrees of methoxy/hydroxypropyl substitution, European Journal of Pharmaceutical Sciences, 9(2):171-184.

Handbook of Pharmaceutical Excipients, 6th Ed, 2009, pp. 326-329.

International Search Report and Written Opinion issued in International Application No. PCT/US2020/034611, date of mailing: Oct. 14, 2020, 45 pages.

International Search Report and Written Opinion issued in International Application No. PCT/US2020/34608, date of mailing: Oct. 14, 2020, 28 pages.

International Search Report and Written Opinion issued in International Application No. PCT/US2020/34609, date of mailing: Oct. 14, 2020, 22 pages.

International Search Report and Written Opinion issued in International Application No. PCT/US2021/039303, date of mailing: Nov. 26, 2021, 19 pages.

International Search Report and Written Opinion mailed Nov. 5, 2018, for International Patent Application PCT/US2018/038067 with International filing date Jun. 18, 2018 (11 pages).

International Search Report issued in an International Application No. PCT/US2021/030450, date of mailing: Sep. 27, 2021, 9 pages.

Kantor, 2000, The Antianginal Drug Trimetazidine Shifts Cardiac Energy Metabolism From Fatty Acid Oxidation to Glucose Oxidation by Inhibiting Mitochondrial Long-Chain 3-Ketoacyl Coenzyme A Thiolase, Circulation Research, 86:580-588.

Kotreka, 2011, Gastroretentive Floating Drug-Delivery Systems: A Critical Review, Critical Reviews in Therapeutic Drug Carrier Systems, 28(1):47-99.

Leriche, 2012, Cleavable linkers in chemical biology, Bioorg. Med. Chem. 20:571-582.

(56) References Cited

OTHER PUBLICATIONS

Levy, 2014, Vasodilators in Acute Heart Failure: Review of the Latest Studies, Curr Emerg Hosp Med Rep, 2 (2): 126-134.

Lopaschuk, 2010, Myocardial Fatty Acid Metabolism in Health and Disease, Phys. Rev. 90:207-258.

Maskova, 2020, Hypromellose—A traditional pharmaceutical excipient with modern applications in oral and oromucosal drug delivery, Journal of Controlled Release, 324:695-727.

Morin, 1998, Evidence for the existence of [3H]-trimetazidine binding sites involved in the regulation of the mitochondrial permeability transition pore, Brit. J. Pharmacol. 123:1385-1394.

Narokha, 2014, Antioidant effect of nicotinic acid on experimental doxorubicin-induced chronic heart failure, Current Topics in Pharmacology, 18:105-111.

Non-Final Office Action issued in U.S. Appl. No. 16/722,691, date of mailing: Aug. 19, 2020, 12 pages.

Pubchem, CID 2223657, Jul. 15, 2005, pp. 1-14.

Pubchem, CID-57503849, Create Date: Aug. 8, 2012, 16 pages.

Reddy, 2006, Lipid Metabolism and Liver Inflammation. II. Fatty liver disease and fatty acid oxidation, Am J Physiol Gastrointest Liver Physiol, 290: G852-G858.

Sabbah, 2005, Metabolic Therapy for Heart Disease: Impact of Trimetazidine, Heart Failure Reviews, 10, 281-288.

Sannino, 2009, Biodegradable Cellulose-based Hydrogels: Design and Applications, Materials, 2:353-373.

Schipke, 1994, Cardiac efficiency, Basic Res. Cardiol. 89:207-40.

Spiekerkoetter, 2010, Mitochondrial fatty acid oxidation disorders: clinical presentation of long-chain fatty acid oxidation defects before and after newborn screening, J Inherit Metab Dis, 33:527-532.

Steggall, 2017, Targeting Metabolic Modulation and Mitochondrial Dysfunction in the Treatment of Heart Failure, Diseases, 5(14):1-18.

Tang, 2009, The Metabolic Approach in Patients with Heart Failure: Effects on Left Ventricle Remodeling, 15(8):850-856.

The Merck Manual List of Diseases https://merckmanuals.com/professional (accessed Jan. 17, 2020), 4 pages.

Trammell, 2016, Nicotinamide riboside is uniquely and orally bioavailable in mice and humans, Nat. Commun. 7:12948, 14 pages.

Visser, 2008, Measuring cardiac efficiency: is it clinically useful? Heart Metab. 39:3-4.

Yuasa, 1988, Pharmacological Studies on the Actions of Trimetazidine and Its Derivatives, The Journal of Kansai Medical University, vol. 40, Issue 1, pp. 89-116.

Zhou, 2012, Trimetazidine Protects against Smoking-Induced Left Ventricular Remodeling via Attenuating Oxidative Stress, Apoptosis, and Inflammation, Plos One, 7:1-7.

\* cited by examiner

METHODS OF SYNTHESIZING 2-[4-[(2,3,4-TRIMETHOXYPHENYL)METHYL]PIPERAZIN-1-YL]ETHYL PYRIDINE-3-CARBOXYLATE

CROSS-REFERENCE TO RELATED APPLICATIONS

This application is a continuation of U.S. application Ser. No. 17/359,762, filed Jun. 28, 2021, which claims the benefit of, and priority to, U.S. Provisional Patent Application No. 63/046,123, filed Jun. 30, 2020, the contents of which are incorporated by reference herein in their entirety.

FIELD OF THE INVENTION

The invention relates to methods of chemical synthesis of the pharmacological agent 2-[4-[(2,3,4-trimethoxyphenyl)methyl]piperazin-1-yl]ethyl pyridine-3-carboxylate.

BACKGROUND

Heart disease is the leading cause of death worldwide, accounting for 15 million deaths across the globe in 2015. In many forms of heart disease, decreased cardiac efficiency stems from changes in mitochondrial energy metabolism. Mitochondria are sub-cellular compartments in which metabolites derived from glucose and fatty acids are oxidized to produce high-energy molecules. Increasing fatty acid oxidation in the heart decreases glucose oxidation, and vice versa. Glucose oxidation is a more efficient source of energy, but in certain types of heart disease, such as angina, heart failure, ischemic heart disease, and diabetic cardiomyopathies, fatty acid oxidation predominates in cardiac mitochondria. As a result, the pumping capacity of the heart is reduced.

SUMMARY

CV-8972, which has the IUPAC name 2-[4-[(2,3,4-trimethoxyphenyl)methyl]piperazin-1-yl]ethyl pyridine-3-carboxylate and the following structure:

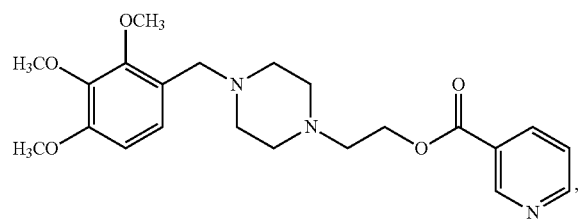

was recently identified as a promising therapeutic candidate for cardiovascular conditions. Prior schemes for synthesis of CV-8972 require formation of a free base form of 2-[4-[(2,3,4-trimethoxyphenyl)methyl]piperazin-1-yl]ethanol, also called CV-8814, and conversion of the free base form of CV-8814 to a hydrochloride salt. In such schemes, CV-8814 must then be converted back to its free base form for coupling to nicotinic acid to form the free base form of CV-8972.

The invention provides a CV-8972 synthesis scheme that bypasses the reversible conversion of CV-8814 between the free base and HCl salt forms. In the schemes provided herein, the free base form of CV-8814 is formed in a reductive amination reaction, and the free base product is used directly as a substrate for coupling to nicotinic acid to form CV-8972. Because fewer steps are required, the synthesis schemes of the invention are simpler, faster, and provide better yields than prior methods of making CV-8972.

In an aspect, the invention provides methods for preparing a compound of Formula (X):

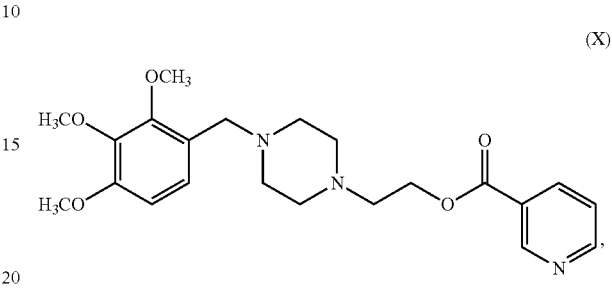

by performing the steps of:
reacting 2,3,4-trimethoxybenzaldehyde and 2-(piperazin-1-yl)ethan-1-ol to produce a free base form of a compound of Formula (IX):

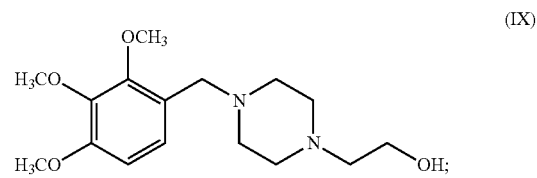 [SMILES: COc1ccc(CN2CCN(CCO)CC2)c(OC)c1OC]

and
reacting the free base form of the compound of Formula (IX) with nicotinic acid to produce the compound of Formula (X), wherein the method does not comprise producing a salt form of the compound of Formula (IX).

The step of reacting 2,3,4-trimethoxybenzaldehyde and 2-(piperazin-1-yl)ethan-1-ol may include one or more solvents, catalysts, or other chemicals. The step of reacting 2,3,4-trimethoxybenzaldehyde and 2-(piperazin-1-yl)ethan-1-ol may include one or more of sodium triacetoxyborohydride, acetic acid, and 2-methyltetrahydrofuran.

The step of reacting 2,3,4-trimethoxybenzaldehyde and 2-(piperazin-1-yl)ethan-1-ol may be performed at a defined temperature. The step of reacting 2,3,4-trimethoxybenzaldehyde and 2-(piperazin-1-yl)ethan-1-ol may be performed at from about 10° C. to about 30° C., from about 15° C. to about 30° C., from about 20° C. to about 30° C., from about 25° C. to about 30° C., from about 10° C. to about 25° C., from about 15° C. to about 25° C., from about 20° C. to about 25° C., from about 10° C. to about 20° C., or from about 15° C. to about 20° C.

The step of reacting 2,3,4-trimethoxybenzaldehyde and 2-(piperazin-1-yl)ethan-1-ol may not include a specific solvent, catalyst, or other chemical. The step of reacting 2,3,4-trimethoxybenzaldehyde and 2-(piperazin-1-yl)ethan-1-ol may not include dichloromethane.

The step of reacting the free base form of the compound of Formula (IX) with nicotinic acid may produce a free base form of the compound of Formula (X).

The step of reacting the free base form of the compound of Formula (IX) with nicotinic acid may include one or more solvents, catalysts, or other chemicals. The step of reacting the free base form of the compound of Formula (IX) with nicotinic acid may include one or more of 1-ethyl-3-(3-dimethylaminopropyl)carbodiimide, 4-(dimethylamino)pyridine, and dichloromethane.

The step of reacting the free base form of the compound of Formula (IX) with nicotinic acid may be performed at a defined temperature. The step of reacting the free base form of the compound of Formula (IX) with nicotinic acid may be performed at from about 15° C. to about 30° C., from about 20° C. to about 30° C., from about 25° C. to about 30° C., from about 15° C. to about 25° C., from about 20° C. to about 25° C., or from about 15° C. to about 20° C.

The method may include converting the free base form of the compound of Formula (X) to a salt form of the compound of Formula (X). The salt form of the compound of Formula (X) may be a HCl salt. The salt form of the compound of Formula (X) may be monohydrate.

The step of converting the free base form of the compound of Formula (X) to the salt form of the compound of Formula (X) may include one or more solvents, catalysts, or other chemicals. The step of converting the free base form of the compound of Formula (X) to the salt form of the compound of Formula (X) may include one or more of HCl and methyl ethyl ketone.

The step of converting the free base form of the compound of Formula (X) to the salt form of the compound of Formula (X) may be performed at a defined temperature. The step of converting the free base form of the compound of Formula (X) to the salt form of the compound of Formula (X) may be performed at from about 40° C. to about 60° C., from about 45° C. to about 60° C., from about 50° C. to about 60° C., from about 55° C. to about 60° C., from about 40° C. to about 55° C., from about 45° C. to about 55° C., from about 50° C. to about 55° C., from about 40° C. to about 50° C., from about 45° C. to about 50° C., from about 40° C. to about 50° C., about 40° C., about 45° C., about 50° C., about 55° C., or about 60° C.

The method may include converting the salt form of the compound of Formula (X) from a first crystal form to a second crystal form. Each of the first and second crystal forms may independently be Form A, Form B, Form C, Form D, or Form E.

The step of converting the salt form of the compound of Formula (X) from a first crystal form to a second crystal form may include one or more of changing the solvent of the salt form of the compound of Formula (X) and incubating the salt form of the compound of Formula (X), at about 60° C.

The method may be performed without the use of one or more solvents, catalysts, or other chemicals. The method may be performed without the use of one or more of dioxane, ethylacetate, or potassium carbonate.

The method may include purifying the free base form of the compound of Formula (IX). The method may include crystallizing the free base form of the compound of Formula (IX).

In another aspect, the invention provides methods of preparing a compound of Formula (X) by performing the steps of:

reacting a compound of Formula (1):

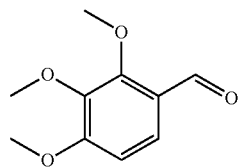

(1)

with a compound of Formula (2):

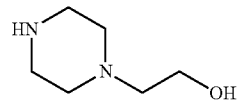

(2)

to produce a free base form of a compound of Formula (IX):

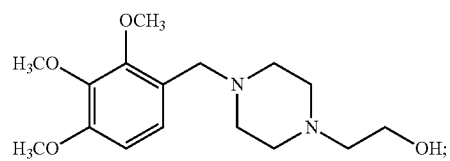

(IX)

reacting the free base form of a compound of Formula (IX) with a compound of Formula (3):

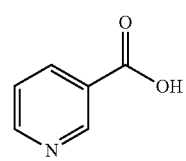

(3)

to produce a free base form of the compound of Formula (X); and converting the free base form of the compound of Formula (X) to a HCl salt of the compound of Formula (X), wherein the method does not comprise producing a salt form of the compound of Formula (IX).

The method may include purifying the free base form of the compound of Formula (IX). The method may include crystallizing the free base form of the compound of Formula (IX).

DETAILED DESCRIPTION

The recently-identified compound CV-8972 holds promise as a therapeutic agent for treating a variety of conditions, including cardiovascular conditions, rheumatic diseases, fibrosis, and cancer. CV-8972, which has the IUPAC name 2-[4-[(2,3,4-trimethoxyphenyl)methyl]piperazin-1-yl]ethyl pyridine-3-carboxylate and the following structure:

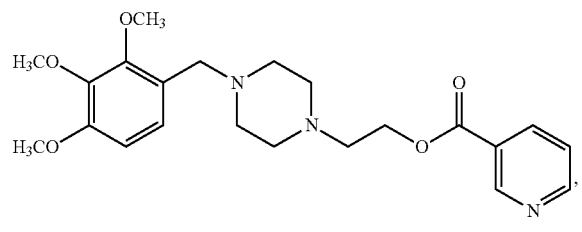 [SMILES: COc1ccc(CN2CCN(CCOC(=O)c3cccnc3)CC2)c(OC)c1OC]

is metabolized in the body into two sets of products that increase mitochondrial energy production in different ways. In an initial reaction, the molecule is split into CV-8814, which has the following structure:

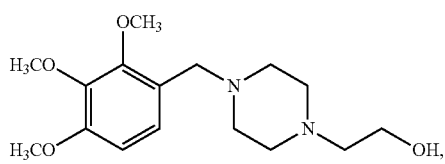

and nicotinic acid. Over time, CV-8814 converted in the body to trimetazidine. Both CV-8814 and trimetazidine inhibit beta-oxidation of fatty acids and therefore shift mitochondrial metabolism toward oxidation of glucose, a more oxygen-efficient source of energy. Nicotinic acid serves as precursor for synthesis of nicotinamide adenine dinucleotide ($NAD^+$). $NAD^+$ promotes mitochondrial respiration to drive ATP synthesis, regardless of whether glucose or fatty acids are used as the carbon source. Thus, the two sets of products that result from breakdown of CV-8972 in vivo act synergistically to stimulate energy production in mitochondria in cardiac tissue and other cell types. CV-8972 and its mechanism of action are described in U.S. Pat. No. 10,556,013, the contents of which are incorporated herein by reference.

U.S. Pat. No. 10,556,013 also provides a scheme for synthesis of CV-8972. The scheme entails formation of a free base form of CV-8814 by reductive amination of 2,3,4-trimethoxybenzaldehyde and 2-(piperazin-1-yl)ethan-1-ol. Due to the difficulty of isolating CV-8814 in a solid form in this prior method, the product of this reaction is then converted to a hydrochloride salt of CV-8814. However, CV-8814 must be converted back to its free base form for use in the esterification reaction with nicotinic acid that produces CV-8972.

The invention provides CV-8972 synthesis schemes in which the free base form of CV-8814 formed as a product in the reductive amination reaction can be used directly as a substrate in the esterification reaction. The invention is based in part on the identification of conditions that improve the stability of CV-8814 free base and allow the free base form to be crystallized. Thus, the schemes provided herein obviate the need to convert CV-8814 from its free base form to a HCl salt and then back to the free base form. Consequently, the invention provides simpler, quicker, and higher-yield methods for making CV-8972.

The invention provides methods for preparing a compound of Formula (X):

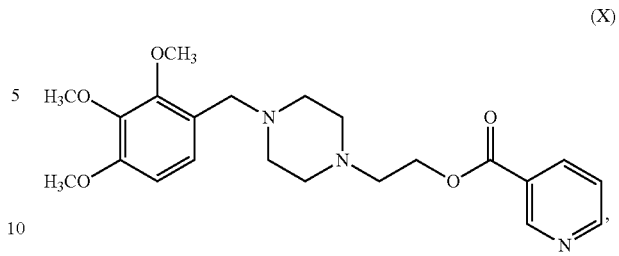

by performing the steps of:
reacting 2,3,4-trimethoxybenzaldehyde and 2-(piperazin-1-yl)ethan-1-ol to produce a free base form of a compound of Formula (IX):

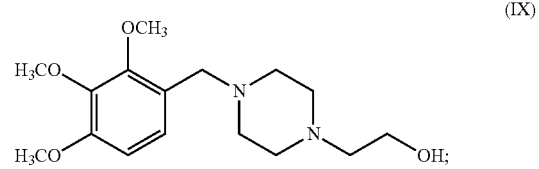 [SMILES: COc1ccc(CN2CCN(CCO)CC2)c(OC)c1OC]

and
reacting the free base form of the compound of Formula (IX) with nicotinic acid to produce the compound of Formula (X),
wherein the method does not comprise producing a salt form of the compound of Formula (IX).

2,3,4-trimethoxybenzaldehyde has the following structure:

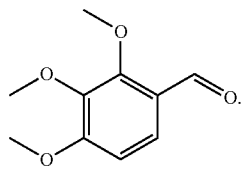

2-(piperazin-1-yl)ethan-1-ol has the following structure:

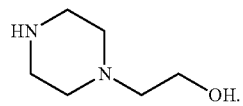

Nicotinic acid has the following structure:

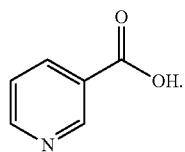

The step of reacting 2,3,4-trimethoxybenzaldehyde and 2-(piperazin-1-yl)ethan-1-ol may include one or more solvents, catalysts, or other chemicals. The step of reacting 2,3,4-trimethoxybenzaldehyde and 2-(piperazin-1-yl)ethan-1-ol may include one or more of sodium triacetoxyborohydride, acetic acid, and 2-methyltetrahydrofuran.

The step of reacting 2,3,4-trimethoxybenzaldehyde and 2-(piperazin-1-yl)ethan-1-ol may be performed at a defined temperature. The step of reacting 2,3,4-trimethoxybenzaldehyde and 2-(piperazin-1-yl)ethan-1-ol may be performed at from about 10° C. to about 30° C., from about 15° C. to about 30° C., from about 20° C. to about 30° C., from about 25° C. to about 30° C., from about 10° C. to about 25° C., from about 15° C. to about 25° C., from about 20° C. to about 25° C., from about 10° C. to about 20° C., or from about 15° C. to about 20° C.

The step of reacting 2,3,4-trimethoxybenzaldehyde and 2-(piperazin-1-yl)ethan-1-ol may not include a specific solvent, catalyst, or other chemical. The step of reacting 2,3,4 trimethoxybenzaldehyde and 2-(piperazin-1-yl)ethan-1-ol may not include dichloromethane.

The step of reacting the free base form of the compound of Formula (IX) with nicotinic acid may produce a free base form of the compound of Formula (X).

The step of reacting the free base form of the compound of Formula (IX) with nicotinic acid may include one or more solvents, catalysts, or other chemicals. The step of reacting the free base form of the compound of Formula (IX) with nicotinic acid may include one or more of 1-ethyl-3-(3-dimethylaminopropyl)carbodiimide, 4-(dimethylamino)pyridine, and dichloromethane.

The step of reacting the free base form of the compound of Formula (IX) with nicotinic acid may be performed at a defined temperature. The step of reacting the free base form of the compound of Formula (IX) with nicotinic acid may be performed at from about 15° C. to about 30° C., from about 20° C. to about 30° C., from about 25° C. to about 30° C., from about 15° C. to about 25° C., from about 20° C. to about 25° C., or from about 15° C. to about 20° C.

The method may include converting the free base form of the compound of Formula (X) to a salt form of the compound of Formula (X). The salt form of the compound of Formula (X) may be a HCl salt. The salt form of the compound of Formula (X) may be monohydrate.

The step of converting the free base form of the compound of Formula (X) to the salt form of the compound of Formula (X) may include one or more solvents, catalysts, or other chemicals. The step of converting the free base form of the compound of Formula (X) to the salt form of the compound of Formula (X) may include one or more of HCl and methyl ethyl ketone.

The step of converting the free base form of the compound of Formula (X) to the salt form of the compound of Formula (X) may be performed at a defined temperature. The step of converting the free base form of the compound of Formula (X) to the salt form of the compound of Formula (X) may be performed at from about 40° C. to about 60° C., from about 45° C. to about 60° C., from about 50° C. to about 60° C., from about 55° C. to about 60° C., from about 40° C. to about 55° C., from about 45° C. to about 55° C., from about 50° C. to about 55° C., from about 40° C. to about 50° C., from about 45° C. to about 50° C., from about 40° C. to about 50° C., about 40° C., about 45° C., about 50° C., about 55° C., or about 60° C.

The compound of Formula (X) may exist in at least five crystal forms: Form A, Form B, Form C, Form D, and Form E. Form A is monohydrate, and Forms B, D, and E are anhydrous. The method may include converting the compound of Formula (X) from a first crystal form to a second crystal form. Each of the first and second crystal forms may independently be Form A, Form B, Form C, Form D, or Form E. The method may include one or more of the following conversions of the compound of Formula (X): from an anhydrous form to a hydrated form; from a hydrated form to an anhydrous form; from one anhydrous form to another; and from one hydrated form to another.

The step of converting the salt form of the compound of Formula (X) from a first crystal form to a second crystal form may include one or more of changing the solvent of the salt form of the compound of Formula (X) and incubating the salt form of the compound of Formula (X), at about 60° C.

The method may be performed without the use of one or more solvents, catalysts, or other chemicals. The method may be performed without the use of one or more of dioxane, ethylacetate, or potassium carbonate.

The method may include purifying the free base form of the compound of Formula (IX). The method may include crystallizing the free base form of the compound of Formula (IX).

EXAMPLES

Example 1

Introduction
CV-8972 was synthesized according to Scheme 1.

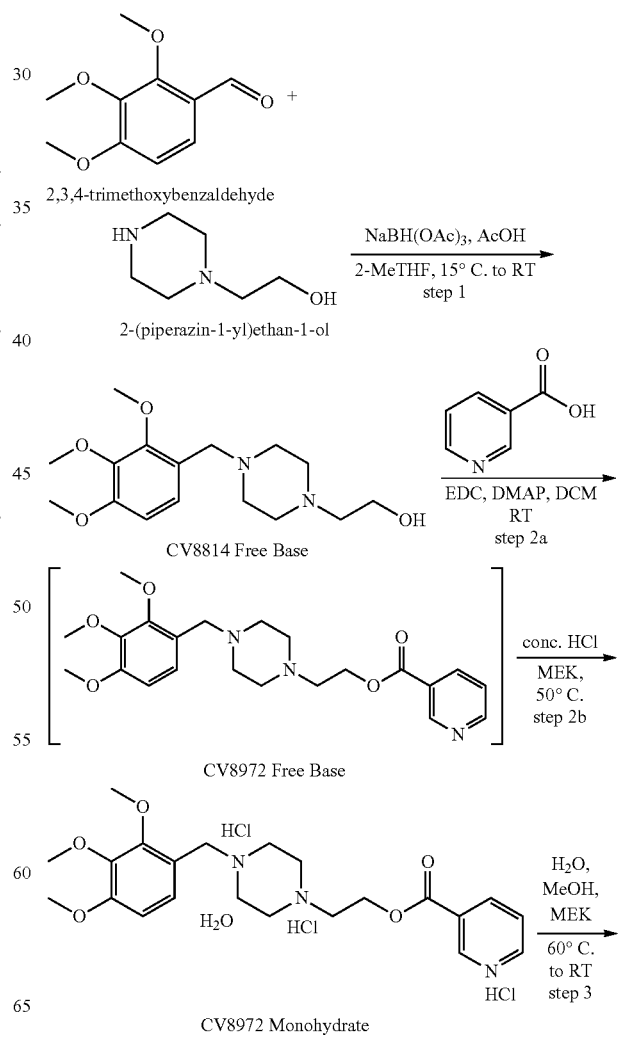

Scheme 1:

-continued

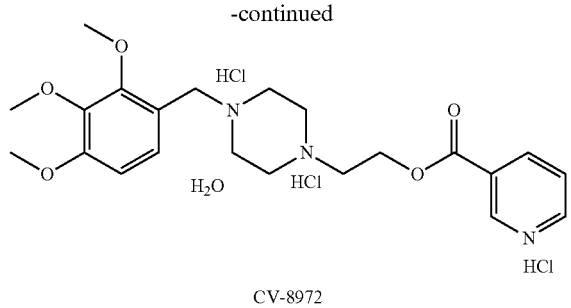

CV-8972

Step 1 is a reductive amination using 2,3,4-trimethoxybenzaldehyde and 2-(piperazin-1-yl)ethan-1-ol starting materials, with sodium triacetoxyborohydride (STAB) as the reductant, in the presence of catalytic acetic acid (AcOH), and 2-methyltetrahydrofuran (2-MeTHF) as solvent. After the reaction is completed, an aqueous workup, solvent exchange to MTBE, and recrystallization from MTBE/n-heptane forms the intermediate CV-8814 Free Base (CV8814 Free Base).

In step 2, CV-8814 Free Base (CV8814 Free Base) undergoes acid coupling with nicotinic acid in the presence of 1-ethyl-3-(3-dimethylaminopropyl)carbodiimide (EDC) and catalytic 4-(dimethylamino)pyridine (DMAP) in dichloromethane (DCM) solvent. After aqueous workup, CV8972 Free Base is formed. Solvent exchange to 2-butanone (MEK) followed by addition into concentrated HCl in MEK forms CV8972 Monohydrate intermediate.

The final step 3 is a form conversion in a mixture of water, methanol, and MEK at 60° C.±5° C. followed by a precipitation by the addition of MEK to obtain the desired form A of final product CV-8972 by XRPD analysis.

Manufacturing Details
Manufacturing details are provided in Table 1.

TABLE 1

| Step# | BOP# | Amount Started (Kg) | Amount Produced (Kg) | Yield (%) | HPLC Purity (%) |
|---|---|---|---|---|---|
| 1 | 2493-1903-00484 | 27.5 kg | 34.0 kg | 76.0% | 100.0% |
| 2 | 2479-1903-00489 | 28.8 kg | 48.6 kg | 96.4% | 99.1% |
| 3 | 2479-1904-00494 | 48.5 kg | 41.7 kg | 86.0% | 99.9% |

Production Details
Step 1, formation of CV8814 Free Base (2493-1903-00487), was performed according to Scheme 2.

Scheme 2

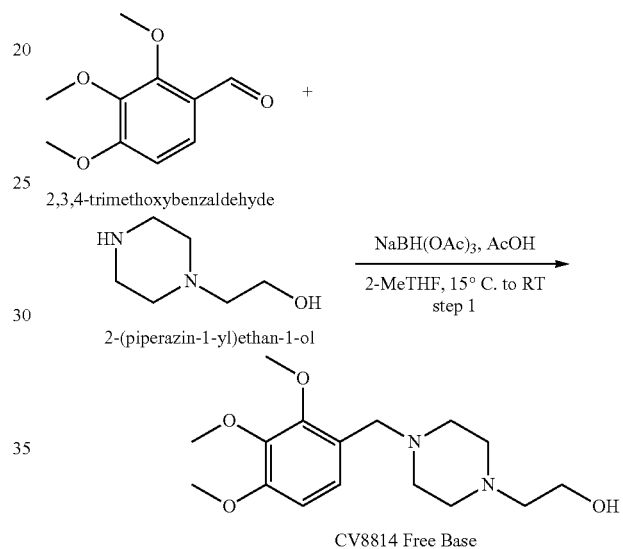

Production details for step 1 are provided in Table 2.

TABLE 2

| Identity Name | Vendor/Grade/ Catalog # | MW g/mol | Equiv. Moles/ mol-LR | Moles moles | Expected Quantity Units | Actual Quantity Used Units |
|---|---|---|---|---|---|---|
| 2,3,4-Trimethoxy-benzaldehyde | Oakwood/98%/ 078721; Chem-Impex/ NA/26868; Chem-Impex/NA/26868 | 196.20 | 1.00 | 140.16 | 27.5 kg | 27.5 kg |
| 1-(2-hydroxyethyl)piperazine | Aldrich/98%/ H28807 | 130.19 | 1.1 | 154.18 | 20.1 kg | 20.0 kg |
| 2-Methyltetrahydrofuran (2-MeTHF) | Aldrich/≥99.5%/ 155810 | N/A | N/A | N/A | 309.5 kg Plus As Needed | 338.3 kg |
| Acetic Acid (AcOH) | Aldrich/≥99%/ A6283 | N/A | N/A | N/A | 1.40 kg | 1.4101 kg |
| Sodium Triacetoxy Borohydride (STAB) | Oakwood/95%/ 044864 | 211.94 | 2.00 | 280.32 | 59.4 kg Plus As Needed | 60.3 kg |
| Sodium Hydroxide solution, 50% in $H_2O$ (50% NaOH in $H_2O$) | Aldrich/50% in $H_2O$/ 415413 | 40 | 6.09 | 853.57 | 68.3 kg | 68.3 kg |
| Sodium Chloride (NaCl) | Aldrich/ACS/ S9888 | N/A | N/A | N/A | 19.0 kg | 19.0 kg |
| Methyl tert-Butyl Ether (MTBE) | Aldrich/ACS/ 443808; Oakwood/ ACS/099538 | N/A | N/A | N/A | 417.3 Plus As Needed | 552.1 kg |

TABLE 2-continued

| Identity Name | Vendor/Grade/ Catalog # | MW g/mol | Equiv. Moles/ mol-LR | Moles moles | Expected Quantity Units | Actual Quantity Used Units |
|---|---|---|---|---|---|---|
| Water | Mediatech/WFI/25-055-X[1]; RMBI/USP/ WPW-USN-2XL | N/A | N/A | N/A | 323.4 kg | 323.4 kg |
| Heptane | Aldrich/99%/ H2198; Oakwood/ ACS/044743; BDH/ ACS/BDH1127 | N/A | N/A | N/A | 159.8 kg | 162.1 kg |
| Nitrogen Gas (house system) | Airgas ≥99% | N/A | N/A | N/A | Quantity Sufficient (QS) | Quantity Sufficient |

1) Sodium Triacetoxy Borohydride (STAB; 60.3 kg; CHP Lot #: 181-190220) and 2-MeTHF (189.2 kg; CHP Lot #: 234-190227) was charged to reactor R-401.
2) The contents of R-401 were agitated and the temperature was adjusted to 15° C.±5° C.
3) 2,3,4-trimethoxybenzaldehyde (27.5 kg; CHP Lot #: 275-190311, 142-190212) and 2 MeTHF (71.1 kg: CHP Lot #: 234-190227) was charged to reactor R-402.
4) Agitation of reactor R-402 was started.
5) 2-(piperazin-1-yl)ethan-1-ol (20.0 kg; CHP Lot #: 173-190220) and 2-MeTHF (47.3 kg; CHP Lot #: 234-190227) was charged to reactor R-402.
6) The contents of reactor R-402 were agitated for at least 5 minutes.
7) Acetic Acid (1.41 kg: CHP Lot #: 151-190214) was charged to reactor R-401 while keeping the temperature of the mixture below 25° C.
8) $T_{max}$=14.4° C.
9) The contents of reactor R-402 were transferred over 1 h 19 min while keeping the temperature of the mixture below 25° C.
10) $T_{max}$=29.2° C. (the temperature went out of range during the addition)
11) The reaction was approved to proceed forward
12) The temperature of the contents of R-401 were adjusted to 20° C.±5° C. and agitated for at least 6 hours at 20° C.±5° C.
13) The contents of R-401 were sampled after approximately 19 hours.
14) Analysis of the sample by QC indicated no peak of 2,3,4-trimethoxybenzaldehyde was detected. (specification≤1.5 area %)
15) The temperature of the contents of R-401 were adjusted to 15° C.±5° C.
16) Water (247.5 kg; CHP Lot #: 232-190227) was charged to R-401 while keeping the temperature below 25° C.
17) $T_{max}$=14.6° C.
18) The temperature of the contents of R-401 was adjusted to 20° C.±5° C. and the contents were agitated for 30 minutes.
19) The contents of R-401 were allowed to settle for 30 minutes.
20) Phase cut was performed with the aqueous layer being transferred to R-402.
21) MTBE (203.8 kg; CHP Lot #: 207-190222) was charged to R-402.
22) The temperature of the contents of R-402 was adjusted to 0° C.±5° C.
23) 50% NaOH (68.3 kg; CHP Lot #: 145-190213, 150-190214) was charged to R-402 while maintaining a temperature below 25° C.
24) $T_{max}$=11.5° C.
25) After complete addition, the temperature of the contents of R-402 was adjusted to 20° C.±5° C.
26) The contents in R-402 were agitated for at least 30 min, followed by allowing the contents to settle for at least 30 min.
27) A phase cut was performed with the aqueous layer being transferred to reactor R-401 and the organic layer remaining in reactor R-402.
28) MTBE (61.0 kg; CHP Lot #: 207-190222) was charged to R-401.
29) The temperature of the contents of R-401 was adjusted to 20° C.±5° C.
30) The contents in R-401 were agitated for at least 15 min, followed by allowing the contents to settle for at least 15 min.
31) A phase cut was performed with the aqueous layer being transferred to a drum and the organic later remaining in reactor R-401.
32) FIO pH check of drummed aqueous layer pH=13.20
33) The contents in R-402 were transferred to R-401.
34) 20% NaCl solution (94.4 kg; NaCl: 19.0 kg, CHP Lot #: 156-190214; Water (75.9 kg; CHP Lot #: 232-190227) was charged to R-401, agitated for at least 15 minutes and allowed to settle for at least 30 minutes.
35) A phase cut was performed with the aqueous layer being transferred to a drum.
36) The solution in R-401 was distilled under reduced pressure while maintaining a temperature <45° C. to approximately ~55 L total volume.
37) MTBE (61.1 kg; CHP Lot #: 207-190222) was charged to R-401.
38) The contents in R-401 were distilled under reduced pressure while maintaining a temperature <45° C. to approximately ~82 L total volume.
39) MTBE (61.1 kg; CHP Lot #: 207-190222) was charged to R-401.
40) The contents in R-101 were distilled under reduced pressure while maintaining a temperature <45° C. to approximately ~82 L total volume.
41) The contents of R-401 were sampled (IPC sample: 2493-1903-00484-85-01) to check the water content of the solution by KF analysis.
42) KF=1.6% (specification≤0.5%)
43) MTBE (61.1 kg; CHP Lot #: 207-190222) was charged to R-401.

44) The contents in R-101 were distilled under reduced pressure while maintaining a temperature <45° C. to approximately ~82 L total volume.
45) The contents of R-401 were sampled (IPC sample: 2493-1903-00484-88-01) to check the water content of the solution by KF analysis.
46) KF=0.8% (specification≤0.5%)
47) MTBE (61.1 kg; CHP Lot #: 207-190222) was charged to R-401.
48) The contents in R-101 were distilled under reduced pressure while maintaining a temperature <45° C. to approximately ~82 L total volume.
49) The contents of R-401 were sampled (IPC sample: 2493-1903-00484-91-01) to check the water content of the solution by KF analysis.
50) KF=0.4% (specification≤0.5%)
51) MTBE (30.9 kg; CHP Lot #: 207-190222) was charged to R-401.
52) The temperature of the contents of R-401 was adjusted to 40° C.±5° C.
53) Heptane (56.3 kg; CHP Lot #: 233-190227) was charged over 8 min to R-401 while maintaining the temperature at 40° C.±5° C.
54) $T_{min}$=38.1° C.
55) A FIO sample (FIO sample: 2493-1903-00484-100-01) was taken to observe the ratio of MTBE:Heptane of the contents in R-401. The ratio was 1.5:6.0.
56) The temperature of the contents of R-401 were adjusted to 28° C.±5° C. (Target 26° C. to 29° C.) over at least 30 min and agitated at that temperature for at least 30 min.
57) Solid formation was observed.
58) The temperature of the contents of R-401 were adjusted to 30° C.±3° C. and agitated for at least 30 min.
59) Heptane (56.4 kg; CHP Lot #: 233-190227) was charged over 24 min to R-401 while maintaining the temperature at 30° C.±5° C.
60) $T_{min}$=30.2° C.
61) The temperature of the contents of R-401 were adjusted to 30° C.±3° C. and agitated for at least 20 min.
62) The temperature of the contents of R-401 were adjusted to 20° C.±5° C. over at least 30 min and agitated for at least 20 min.
63) The temperature of the contents of R-401 were adjusted to 5° C.±5° C. over at least 30 min and agitated for at least 30 min.
64) The solid was collected on Filter-FD-400.
65) The contents of Filter-FD-400 were washed with cold heptane (49.4 kg; CHP Lot #: 233-190227).
66) The contents of Filter-FD-400 were dried under vacuum at ≤25° C. with a stream of N2 for at least 16 hours.
67) An IPC sample (IPC sample: 2493-1903-00484-122-01) was submitted to QC for LOD.
LOD=0.20% (specification≤0.5%)
68) The product CV-8814 Free Base (CV8814 Free Base) was double bagged, goose necked, and weighed.
69) Analysis of dried material (IPC sample: 2493-1903-00484-122-01):
Appearance: White to off white solid
Weight: 34.0 kg (78.0% yield)
HPLC Purity=100.0%
1H NMR: conforms to structure
70) A 5 kg portion of CV-8814 Free Base (CV8814 Free Base) was removed from the bulk material double bagged, goose necked, and set aside for release under the Lot #2493-1903-00484.

Step 2, formation of CV8972 Monohydrate (2479-1903-00489), was performed according to Scheme 3.

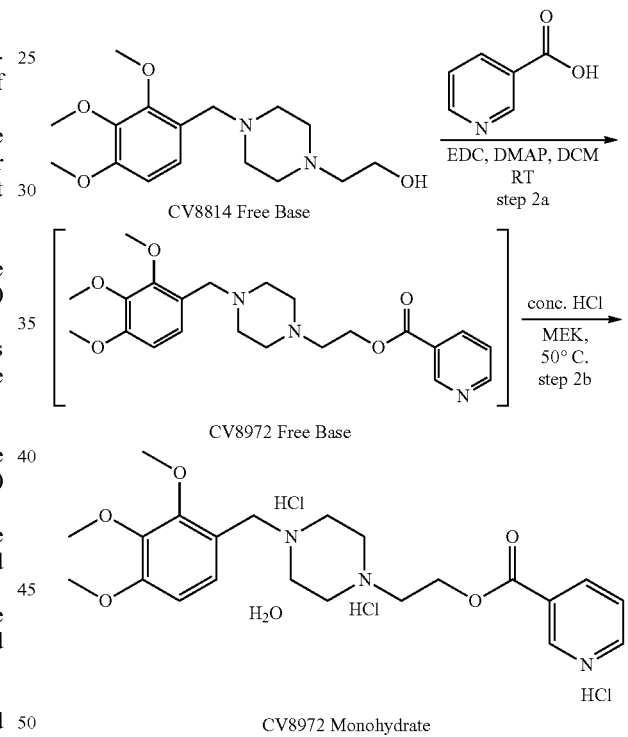

Scheme 3

Production details for steps 2a and 2b are provided in Table 3.

TABLE 3

| Identity Name | Vendor/Grade/ Catalog # | MW g/mol | Equiv. Moles/ mol-LR | Moles moles | Expected Quantity Units | Actual Quantity Used Units |
|---|---|---|---|---|---|---|
| CV8814 Free Base (IMB-1028814) | CHP/NA/CHP Lot # 2493-1903-00484 | 310.39 | 1.00 | 92.79 | 28.8 kg | 28.8 kg |
| Nicotinic Acid | Aldrich/≥98%/ N4126; Alfa Aesar/ 99%/A12683 | 123.11 | 1.5 | 139.19 | 17.1 kg | 17.1 kg |

TABLE 3-continued

| Identity Name | Vendor/Grade/ Catalog # | MW g/mol | Equiv. Moles/ mol-LR | Moles moles | Expected Quantity Units | Actual Quantity Used Units |
|---|---|---|---|---|---|---|
| CV8814 Free Base (IMB-1028814) | CHP/NA/CHP Lot # 2493-1903-00484 | 310.39 | 1.00 | 92.79 | 28.8 kg | 28.8 kg |
| Nicotinic Acid | Aldrich/≥98%/ N4126; Alfa Aesar/ 99%/A12683 | 123.11 | 1.5 | 139.19 | 17.1 kg | 17.1 kg |
| Dichloromethane (DCM) | Aldrich/ACS/ D65100 | N/A | N/A | N/A | 536.2 kg | 533.4 kg |
| EDC | Oakwood/99%/ 024810; Chem-Impex/ ≥99%/00050 | 191.71 | 1.5 | 139.19 | 26.7 kg | 26.7 kg |
| 4-(Dimethylamino)pyridine (DMAP) | Aldrich/≥99%/ 107700 | 122.17 | 0.15 | 13.92 | 1.70 kg | 1.70 kg |
| Hydrochloric Acid (Conc HCl) | Avantor/ACS/ 2612-X[1] | 36.46 | 3.3 | 306.21 | 30.2 kg | 30.2 kg |
| Sodium Bicarbonate (NaHCO$_3$) | Aldrich/ACS/ S6014 | N/A | N/A | N/A | 4.0 kg | 4.00 kg |
| Water | Mediatech/WFI/ 25-055-X[1]; RMBI/ USP/ WPW-USN-2XL | N/A | N/A | N/A | 140.9 kg | 140.4 kg |
| Methyl Ethyl Ketone (MEK) | Oakwood/99.9%/ 075238 | N/A | N/A | N/A | 858.0 kg | 857.8 kg |
| Nitrogen Gas (house system) | Airgas ≥99% | N/A | N/A | N/A | Quantity Sufficient (QS) | Quantity Sufficient |

1) Nicotinic Acid (17.1 kg, CHP Lot #201-190222) and DCM (153.0 kg, CHP Lot #328-190326) were charged to reactor R-401
2) The contents of R-401 was agitated and the temperature was adjusted to 15±5° C.
3) CV8814 Free Base (28.8 kg, CHP Lot #2493-1903-00484), EDC (26.7 kg, CHP Lot #147-190213), DMAP (1.70 kg, CHP Lot #152-190214), and DCM (306.6 kg, CHP Lot #328-190326) were charged to reactor R-402.
4) The contents of the R-402 were agitated for at least 20 minutes.
5) The contents of R-402 were transferred to R-401 over at least 30 minutes while keeping the temperature below 25° C.
6) $T_{max}$=20.0° C.
7) The temperature of the contents of R-401 were adjusted to 20±5° C. and was agitated for at least 16 hours.
8) The contents of R-401 were sampled after approximately 16 hours.
9) Analysis of the sample by QC indicated 0% (0.05%) of CV-8814 Free Base (CV8814 Free Base) with respect to CV8972 was detected (Specification: ≤1% CV8814 Free Base).
10) The contents of the R-401 were adjusted to 10±5° C.
11) Water (29.2 kg, CHP Lot #329-190326) was slowly added while keeping the temperature below 25° C.
12) $T_{max}$=12.3° C.
13) The temperature of the contents of R-401 was adjusted to 20±5° C., agitated for at least 15 min and allowed to settle for at least 15 min.
14) Phases were separated.
15) The lower organic layer containing product was transferred to reactor R-402. The aqueous layer was sent to a drum.
16) Water (29.0 kg, CHP Lot #329-190326) was charged to the reactor.
17) The biphasic mixture was agitated for 15 min and allowed to settle for 15 min.
18) Phases were separated.
19) The organic layer containing product was transferred to reactor R-401. The aqueous layer was sent to a drum.
20) 8% NaHCO$_3$ aqueous solution (Sodium Bicarbonate, 4.0 kg, CHP Lot #192-190221; Water, 53.2 kg, CHP Lot #329-190326) was added to the reactor.
21) The mixture was agitated for at least 15 min and allowed to settle for at least 15 min.
22) Phases were separated.
23) The lower organic layer containing product was transferred to reactor R-402. The aqueous layer was sent to a drum.
24) Water (29.0 kg, CHP Lot #329-190326) was added to the reactor.
25) The mixture was agitated for at least 15 min and allowed to settle for at least 15 min.
26) R-401 was cleaned with Water (17.6 kg, CHP Lot #329-190326) and MEK (5.9 kg, CHP Lot #330-190326) and dried with a stream of N2.
27) Phases were separated.
28) The lower organic layer containing product was transferred to reactor R-401. The aqueous layer was sent to a drum.
29) The contents of R-401 were concentrated under reduced pressure to approx. 72 L keeping the temperature below 45° C.
30) $T_{max}$=32.0° C.
31) MEK (139.0 kg, CHP Lot #330-190326) was charged to R-401.
32) The contents of R-401 were concentrated under reduced pressure to approx. 72 L keeping the temperature below 45° C.
33) $T_{max}$=32.0° C.
34) MEK (139.1 kg, CHP Lot #330-190326) was charged to R-401.

35) The contents of R-401 were concentrated under reduced pressure to approx. 72 L keeping the temperature below 45° C.
36) $T_{max}$=29.2° C.
37) FIO 1H NMR to determine the DCM:MEK ratio was taken. DCM:MEK=1:214.9
38) MEK (185.5 kg, CHP Lot #330-190326) was charged to R-401.
39) MEK (208.7 kg, CHP Lot #330-190326) and conc. HCl (30.2 kg, CHP Lot #274-190311) were charged to a cleaned R-402.
40) The temperature of the contents of reactor was adjusted to 25±5° C.
41) The contents of R-401 were transferred to R-402 over approx. 1 hour while maintaining a temperature below 35° C.
42) $T_{max}$=27.2° C.
43) The temperature of the contents of R-402 was heated to 50±5° C. and was agitated for at least 1 hour.
44) The temperature of the contents of the reactor was cooled to 20±5° C. over 2 hours.
45) The contents of the reactor were agitated at 20±5° C. for 15 hours.
46) The solid was filtered.
47) The filter cake was rinsed with MEK (58.0 kg, CHP Lot #330-190326).
48) The filter cake was rinsed with MEK (58.0 kg, CHP Lot #330-190326).
49) The wet cake was dried in tray dryer 20-25° C. without nitrogen bleed for at least 16 hours.
50) An IPC sample (IPC sample: 2479-1903-00489-87-01) was submitted to QC for KF.
Water content (Specification: ≤4% by cKF): 3.3%
51) The product CV8972 Monohydrate was doubled bagged, goose necked, and weighed.

52) Analysis of the dried material (IPC sample: 2479-1903-00489-87-01):
Appearance: White to off-white solid
Weight: 48.6 kg (96.4% yield)
1H NMR: conforms to structure
HPLC purity (area %): 99.1%
FIO Residual Solvents GC Analysis:
2-MeTHF: No Peak
DCM: No Peak
MTBE: No Peak
Heptane: No Peak
MEK: 343 ppm
Acetic Acid: 874 ppm Step 3, formation of CV-8972 (2479-1904-00494), was performed according to Scheme 4.

Scheme 4

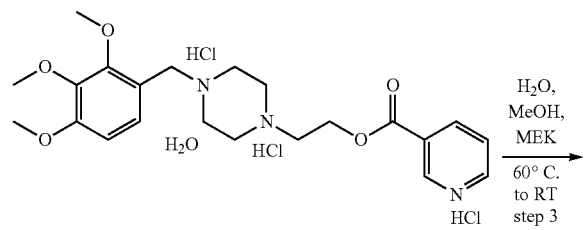

CV8972 Monohydrate

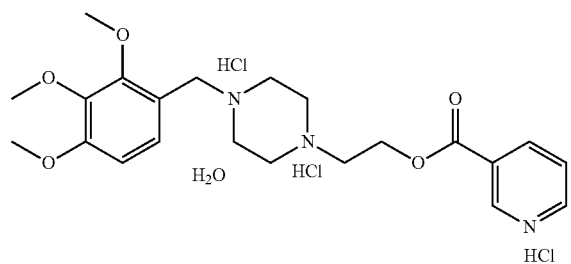

CV-8972

Production details for step 3 are provided in Table 4.

TABLE 4

| Identity Name | Vendor/Grade/ Catalog # | MW g/mol | Equiv. Moles/ mol-LR | Moles moles | Expected Quantity Units | Actual Quantity Used Units |
| --- | --- | --- | --- | --- | --- | --- |
| CV8972 monohydrate | CHP/NA/CHP Lot #2479-1903-00489 | 542.88 | 1 | 89.34 | 48.5 kg | 48.5 kg |
| Methanol | Aldrich/ACS/179337; Pharmco/WORLD/ 339WORLD-X[1]; BDH/ACS/ BDH1135 | N/A | N/A | N/A | 230.5 kg | 230.5 kg |
| Methyl Ethyl Ketone (MEK) | Oakwood/99.9%/075238 | N/A | N/A | N/A | 1147.8 kg | 1149.4 kg |
| Water | Mediatech/WFI/25-055-X[1]; RMBI/USP/WPW-USN-2XL | N/A | N/A | N/A | 72.8 kg | 72.5 kg |
| Nitrogen Gas (house system) | Airgas ≥99% | N/A | N/A | N/A | Quantity Sufficient (QS) | Quantity Sufficient |

1) CV8972 monohydrate (48.5 kg, CHP Lot #2479-1903-00489), Water (48.5 kg, CHP Lot #329-190326), Methanol (19.2 kg, CHP Lot #379-190404), and MEK (39.0 kg, CHP Lot #330-190326) were charged respectively to a reactor R-402.
2) The contents of the R-402 was adjusted to 20° C.±5° C. and agitated until a solution was obtained.
3) The contents of R-402 were transferred to R-401 through a 0.45 micron in-line filter.
4) Water (24.0 kg, CHP Lot #329-190326) and Methanol (19.2 kg, CHP Lot #379-190404) were charged to R-402 and transferred to R-401 through a 0.45 micron in-line filter.

5) Methanol (192.1 kg, CHP Lot #379-190404) was charged to R-401 through a 0.45 micron in-line filter.
6) The temperature of the contents of R-401 was adjusted to 60±5° C.
7) MEK (899.6 kg, CHP Lot #330-190326; 380-190404) was charged to R-401 through a 0.45 micron in-line filter over approx. 2 hours while maintaining a temperature of 60±5° C.
8) The contents of R-401 were agitated at 60±5° C. for at least 4 hours.
9) The temperature of R-401 was adjusted to 20±5° C. over at least 3 hours.
10) The contents of R-401 were agitated at 20±5° C. for approx. 9 hours.
11) The contents of R-401 were sent to a filter.
12) The filter cake was rinsed with MEK (105.4 kg, CHP Lot #380-190404).
13) The filter cake was rinsed with MEK (105.4 kg, CHP Lot #380-190404).
14) The wet cake were dried on filter with vacuum for at least 30 minutes.
15) The wet cake was packaged into a filer dryer and dried under reduced pressure at ≤30° C. for at least 12 hours.
16) An IPC sample (IPC sample: 2479-1904-00494-32-01) was submitted to QC for KF and Residual Solvent GC.
Water content (Specification: 2.8-3.8% by cKF)=3.5%
Residual Solvent GC Analysis (Specification: MeOH≤3000 ppm; MEK≤5000 ppm) MeOH=215 ppm; MEK=185 ppm
17) The product CV-8972 was double bagged, goose necked, and weighed.
18) Analysis of the dried material (IPC sample: 2479-1904-00494-32-01)
Appearance: White to off-white solid
Weight=41.7 kg (86.0% yield)
HPLC purity (area %)=99.9%
   Known Impurities:
      Nicotinic Acid: No Peak
      DMAP: No Peak
      CV8814: 0.1%
      2,3,4-Trimethoxy Benzaldehyde: No Peak
      Trimetazidine: No Peak
      CV-10099: No Peak
      CV-10046: No Peak
      XRPD: Conforms to Form A
      Chloride Ion content: 19.4%
      1H NMR: conforms to structure

CONCLUSION

The results provided above show that CV-8972 can be synthesized using Scheme 1. The reductive amination in step 1 using 2,3,4-trimethoxybenzaldehyde and 2-(piperazin-1-yl)ethan-1-ol starting materials, sodium triacetoxyborohydride (STAB) as the reductant, catalytic acetic acid (AcOH), and 2-methyltetrahydrofuran (2-MeTHF) gave a 78.0% yield of CV-8814 Free Base (CV8814 Free Base) with 100.0% purity by HPLC after aqueous workup, solvent exchange, and crystallization. A 5 kg portion of CV-8814 Free Base (CV8814 Free Base) was diverted from the synthesis for release. The step 2 coupling of CV8814 Free Base with nicotinic acid in the presence of EDC and catalytic DMAP in DCM went to complete conversion to CV-8972 Free Base by HPLC IPC. Solvent exchange to MEK and addition into concentrated HCl in MEK afforded CV8972 Monohydrate in a 96.4% yield with 99.1% purity by HPLC. The final form conversion in step 3 was completed by heating CV8972 Monohydrate to 60° C.±5° C. in a mixture of water, methanol, and MEK and precipitating out with the addition of MEK. The white solid CV-8972 was obtained as form A confirmed by XRPD analysis, in an 86.0% yield with 99.9% purity by HPLC. The overall yield of the GMP synthesis of CV-8972 was 64.7%. The final amount of CV-8972 produced was 41.7 kg.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A method for preparing a compound of Formula (X):

(X)

the method comprising the steps of:
   reacting a compound of Formula (1):

(1)

with a compound of Formula (2):

(2)

with sodium triacetoxyborohydride, in the presence of acetic acid and 2-methyltetrahydrofuran to produce a free base form of a compound of Formula (IX):

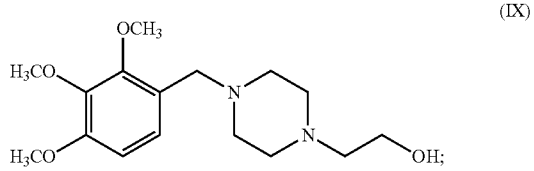 [SMILES: COc1ccc(CN2CCN(CCO)CC2)c(OC)c1OC]

(IX)

and reacting the free base form of a compound of Formula (IX) with a compound of Formula (3):

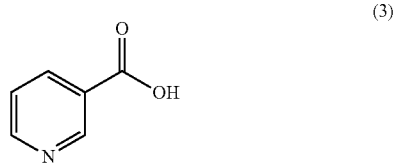

(3)

in the presence of 1-ethyl-3-(3-dimethylaminopropyl)carbodiimide and 4-(dimethylamino)pyridine in dichloromethane to produce the compound of Formula (X).

2. The method of claim 1, wherein the step of reacting the free base form of the compound of Formula (IX) with the compound of Formula (3) produces a free base form of the compound of Formula (X).

3. The method of claim 2, wherein the method further comprises converting the free base form of the compound of Formula (X) to a salt form of the compound of Formula (X).

4. The method of claim 3, wherein the salt form of the compound of Formula (X) is monohydrate.

5. The method of claim 3, further comprising converting the free base form of the compound of Formula (X) to a HCl salt of the compound of Formula (X).

6. The method of claim 3, wherein the step of converting the free base form of the compound of Formula (X) to the salt form of the compound of Formula (X) is performed at about 50° C.

7. The method of claim 3, wherein the method further comprises converting the salt form of the compound of Formula (X) from a first crystal form to a second crystal form.

8. The method of claim 7, wherein the step of converting the salt form of the compound of Formula (X) from the first crystal form to the second crystal form comprises one selected from the group consisting of precipitating the salt form of the compound of Formula (X), changing the solvent of the salt form of the compound of Formula (X), and incubating the salt form of the compound of Formula (X), at about 60° C.

9. The method of claim 1, wherein the step of reacting the compound of Formula (1) and the compound of Formula (2) is performed at from about 15° C. to about 25° C.

10. The method of claim 1, wherein the step of reacting the compound of Formula (1) and the compound of Formula (2) does not comprise dichloromethane.

11. The method of claim 1, further comprising a solvent exchange to Methyl tert-Butyl Ether (MTBE), and recrystallization from MTBE/n-heptane after the step of reacting the compound of Formula (1) and the compound of Formula (2) is complete to form the free base form of a compound of Formula (IX).

12. The method of claim 1, wherein the step of reacting the free base form of the compound of Formula (IX) with the compound of Formula (3) is performed at from about 20° C. to about 25° C.

13. The method of claim 1, wherein the method does not comprise producing a salt form of the compound of Formula (IX).

14. The method of claim 1, wherein the method does not comprise use of dioxane, ethylacetate, or potassium carbonate.

* * * * *